US006294155B1

(12) United States Patent
Thomas et al.

(10) Patent No.: US 6,294,155 B1
(45) Date of Patent: Sep. 25, 2001

(54) ABRASIVE SILICA COMPOSITIONS AND DENTIFRICE COMPOSITIONS PREPARED THEREFROM

(75) Inventors: Michael Bruce Thomas, Pasadena; Michael Vance Ernest, Catonsville; Sandra Joan Kempske, Baltimore, all of MD (US)

(73) Assignee: W. R. Grace & Co. -Conn., Columbia, MD (US)

( * ) Notice: Subject to any disclaimer, the term of this patent is extended or adjusted under 35 U.S.C. 154(b) by 0 days.

(21) Appl. No.: 09/056,688

(22) Filed: Apr. 8, 1998

(51) Int. Cl.$^7$ ...................................................... A61K 7/16
(52) U.S. Cl. ............................................. 424/49; 423/339
(58) Field of Search ............................... 424/49; 423/335, 423/339

(56) References Cited

U.S. PATENT DOCUMENTS

| | | |
|---|---|---|
| 3,670,076 | 6/1972 | Muhler . |
| 3,957,968 | 5/1976 | Cordon . |
| 4,108,978 | 8/1978 | Mazzanobile et al. . |
| 4,153,680 | 5/1979 | Seybert . |
| 4,303,641 | 12/1981 | De Wolf, II . |
| 4,346,071 * | 8/1982 | Dent et al. .............................. 424/49 |
| 4,474,824 * | 10/1984 | DeWolf, II et al. ................... 424/49 |
| 4,618,488 * | 10/1986 | Maeyama et al. ..................... 424/49 |
| 4,631,184 * | 12/1986 | Winyall et al. ........................ 424/49 |
| 4,632,826 | 12/1986 | Plöger et al. . |
| 4,633,701 | 1/1987 | Einlehner . |
| 4,863,722 | 9/1989 | Rosenthal . |
| 4,956,167 * | 9/1990 | Aldcroft et al. ...................... 423/339 |
| 5,108,734 | 4/1992 | Colodney et al. . |
| 5,277,888 | 1/1994 | Baron et al. . |
| 5,310,543 * | 5/1994 | Dawson ................................. 424/49 |
| 5,447,704 * | 9/1995 | Aldcroft et al. ...................... 423/339 |
| 5,589,160 | 12/1996 | Rice . |
| 5,603,920 | 2/1997 | Rice . |
| 5,651,958 | 7/1997 | Rice . |
| 5,658,553 * | 8/1997 | Rice ...................................... 424/49 |
| 5,676,932 * | 10/1997 | Wason et al. ......................... 424/49 |
| 5,858,909 * | 1/1999 | Welsh et al. ......................... 502/243 |
| 5,869,028 * | 2/1999 | McGill et al. ........................ 424/49 |
| 5,939,051 * | 8/1999 | Santalucia et al. ................... 424/49 |

FOREIGN PATENT DOCUMENTS 9609033   3/1996   (WO) .

OTHER PUBLICATIONS

Size Enlargement of Particles. Kirk–Othmer Encyclopedia of Chemical Technology, Third Edition. John Wiley & Sons. N.Y. vol. 21:pp. 106–131. (1983).*

* cited by examiner

Primary Examiner—Robert H. Harrison
(74) Attorney, Agent, or Firm—Charles A. Cross

(57) ABSTRACT

Silica compositions for abrasive systems in dentifrice formulations are disclosed. The silica abrasive system comprises (a) silica gels having a median particle size below 7 microns, a pH of from about 6 to about 11 and powder RDA's of from 100 to about 200 and (b) silica gels or precipitates having a median particle size of 7 microns or greater and powder RDA's of from 50 to about 180. Silica (a) is preferably prepared by contacting a hydrous silica gel with an alkaline medium. Dentifrice compositions comprising the abrasive system has an RDA of 150 or less and PCR's of at least 80 and up to about 150, and an REA of less than about 30 (as measured on the IU scale).

11 Claims, No Drawings

ABRASIVE SILICA COMPOSITIONS AND DENTIFRICE COMPOSITIONS PREPARED THEREFROM

BACKGROUND OF THE INVENTION

1. Field of the Invention

This invention relates to silica compositions useful as an abrasive system in a dentifrice. The invention also relates to dentifrices, preferably toothpastes, which effectively clean teeth without a high degree of dentin and/or enamel abrasion.

2. Relevant Art

Dentifrices, e.g., such as toothpastes, are used to clean teeth. In particular, dentifrices aid in the removal of food particles, the removal of discoloration caused by substances such as tobacco or tea, and the removal of firmly adhering bacterial films, referred to as plaque, from the surface of the teeth. Abrasive substances, also referred to herein as abrasive systems, are formulated in the toothpaste as the primary cleaning agent.

To achieve cleaning, the abrasive systems in dentifrices have to provide a certain degree of abrasiveness with respect to the surface of the teeth. It is important, however, that abrasiveness with respect to dental enamel and dentine be at an acceptably low level to prevent the surface of the teeth from being damaged by the daily use of the toothpaste. The rate of enamel removal through brushing should not exceed the rate at which it is replenished through natural remineralization processes.

The abrasive system used should also be compatible with the other components of the toothpaste. It should lend itself to processing with water, humectants and consistency regulators to form a ductile paste readily dispensable from tubes or dispensers and should not adversely affect known caries inhibitors, for example, fluoride carriers, such as NaF or Na monofluorophosphate, even in the event of prolonged storage.

As illustrated in U.S. Pat. No. 3,957,968, toothpastes containing a combination of alpha-aluminum oxide (corundum) and a second abrasive having a Mohs hardness of less than about 6 are said to have good cleaning and polishing effects. Alpha-aluminum oxide, which has a Mohs hardness of 9, has a relatively strong abrasive effect on dental enamel. To reduce the enamel abrasion, certain calcium, magnesium or sodium salts have been added to a dentifrice containing the aforementioned abrasives.

U.S. Pat. No. 4,303,641 discloses an alkaline treatment for increasing the abrasiveness, and as a result its cleaning performance, of dentifrice silica gel compositions without employing the processing and drying steps typically used to prepare prior art gels. It is noted that treating silica gels with alkaline materials enhances the cleaning performance of the gels as evidenced by increased Radioactive Dentine Abrasion (RDA), defined later below. The Examples in this patent illustrate the alkaline treatment with gels having average particle sizes greater than 10 microns, e.g., about 14–16 microns. The RDA values shown for these alkaline treated gels, however, are quite high as evidenced by "powder" RDA's which this patent reports to be over 1,000 (and over 200 if measured using RDA methods disclosed herein) for some samples. This indicates that the alkaline treated gels exhibit a high degree of abrasiveness on dentin surfaces.

Non-alkaline treated silica xerogel abrasives are also well known in the art. Such gels are prepared to have median particle sizes in the range of 1 to 100 microns. Typically, these gels have particle sizes from 10 to 50 microns, depending on the 'grittiness' desired. The aforementioned '641 patent discloses that non-alkaline treated silica gels are effective polishing and cleaning agents while causing low amounts of damage to underlying tooth materials such as dentin and enamel. However, the aforementioned '641 patent also discloses that more effective abrasives are achieved via alkaline treatment of such silica gels.

U.S. Pat. No. 5,651,958 discloses using a combination of silicas in dentifrices to balance cleaning with minimal abrasion to dentin and enamel surfaces. The '958 patent discloses combining precipitated silica having a narrow particle size range distribution of soft particles having a mean value ranging from 8 to 14 microns with a silica gel in which 70% of the gel particles have a diameter below 25 microns and a Radioactive Dentin Abrasion from 62 to about 100. It is noted that the gel silica particles have an Einlehner hardness from about 3 to about 15 for abrasive to a brass screen.

U.S. Pat. No. 5,589,160 discloses a combination of two precipitated silicas to be used as a dentifrice abrasive. One of the precipitated silicas has a mean particle size of about 5 to 11 microns and an Einlehner hardness of 0.8 to 2.5 for abrasive to a brass screen. The other precipitated silica has a mean particle size of from about 5 to about 11 and an Einlehner hardness from about 3 to about 8 for abrasive to a brass screen.

U.S. Pat. No. 3,670,076 discloses a combination of relatively small and large alumina particles as providing superior abrasives and cleaning.

The above-mentioned measures, however, have not completely solved the problem of obtaining effective cleaning without the excessive abrasion of dental enamel. Workers in the art have continued to search for dentifrices containing abrasive systems which have reduced abrasion of dental enamel, but still effect acceptable cleaning.

SUMMARY OF THE INVENTION

Accordingly, an object of the present invention is to provide suitable dentifrices which, although achieving an optimal cleaning of teeth, can have only a mild abrasive effect. It has been unexpectedly found that such a composition is prepared from a silica composition comprising:

(a) silica gel (i) having a median particle size below 7 microns, (ii) a pH of from about 6 to about 11, and (iii) a hardness defined by powder RDA of 100 to 200, and a PCR of 100 to 150 when said silica (a) is formulated by itself into a dentifrice paste; and (b) silica gel or precipitated silica having a median particle size of 7 microns or greater and having a hardness defined by a powder RDA of about 50 to 180, and a PCR of about 80 to 105 when said silica (b) is formulated by itself in a dentifrice paste, further wherein the weight ratio of (b) to (a) is at least 1:1. Dentifrice compositions comprising (a) and (b) have an RDA of about 150 or below and a PCR of at least 80 and up to about 150, and an REA of less than about 30 (as measured on the IU scale). Silica gel (a) is preferably prepared by contacting a hydrous gel with an alkaline material.

The cleaning performance of silicas (a) and (b) combined is unexpected from cleaning performances of compositions comprising either (a) or (b) alone. For example, abrasives that exhibit a high degree of cleaning are also usually high in dentin or enamel abrasion. As disclosed in the above referenced U.S. Pat. No. 4,303,641, while the silica gels defined in (a) are effective for cleaning performance as a result of the alkaline treatment of hydrous gels, these materials have relatively high abrasion as defined by RDA. Conversely, while dentifrices comprising silicas defined by (b) are generally less abrasive than (a), there is room for improving its cleaning. Applicants have discovered, however, that lower RDA's and improved cleaning performance, as shown by improved PCR's, are obtained by combining (a) and (b). Indeed, silica (b) is widely used for abrasive systems in dentifrice and such systems can easily be improved by combining silica (a) according to this invention with prior art silica abrasives.

DETAILED DESCRIPTION OF PREFERRED EMBODIMENTS

The silica gels defined by (a) can be a hydrogel, xerogel, or aerogel. A preferred embodiment is a hydrous gel which is described in U.S. Pat. No. 4,303,641, the contents of which are incorporated by reference. Such hydrous gels may be prepared from acid set silica hydrogels produced by reacting alkali metal silicate and mineral acids, e.g., sulfuric acid, in aqueous mediums. The acid and silicate are mixed under conditions sufficient to form a sol which in turn converts into a hydrogel. The gel is further aged and washed using conventional techniques to produce a gel having a pH from 2.5 to about 5. The washed gel generally contains less than 5 weight percent total salts, e.g., 0.05 to about 3% $Na_2O$ and 0.05 to 3 weight % $SO_4$, based on the dry weight of the gel.

The washed silica hydrogel generally has a total volatiles content, as measured by loss on ignition at 954° C., of from 60 to about 75 weight percent. The hydrogel is then dried and ground to the desired median particle size. For the purposes of this invention, the hydrogel should preferably be dried to a total volatiles content of from about 5 to about 30 weight percent, and preferably 15 to about 25 weight percent. Oven drying, rotary drying, cascade drying or some other known drying method may be employed. While gels having higher total volatiles content can be used to achieve the desired cleaning, the advantages of lower volatiles level abrasives are lower density and less microbial susceptibility.

Silica gel (a) also should be ground to have a median particle size which is smaller than the median particle size of silica gel (b). In general, the median particle size for (a) is less than 7 microns and preferably less than 4 microns. An especially preferred embodiment of (a) has a median particle size of about 2 to about 3 microns. Generally, silica gel (a) will not have a median particle size less than 0.1 micron.

In a preferred embodiment, the silica hydrogel is simultaneously dried and ground in a mill in order to provide the desired water content and median particle size suitable for use in dentifrice compositions. Suitable mills include pulverizers, impact mills, classifying mills, and fluidized energy mills such as air mills, opposed jet mills and fluid bed jet mills.

The hardness, i.e., abrasiveness, of silica gel (a) is enhanced by contacting the gel with a source of alkalinity. The alkaline source may be, for example, an alkali metal hydroxide, or an alkali metal carbonate. Ammonias and organic amines are also included as suitable alkaline materials. Preferably, the silica gel is contacted with sodium carbonate. Other suitable alkaline materials include sodium hydroxide, ammonium mediums, such as gaseous ammonia, aqueous ammonia, or other aqueous mediums containing, for example, aliphatic amines, particularly alkylamines and alkylene diamines, such as ethyl amine, ethylene diamine, propyl amine, propylene diamine, diethyleneamine, and the like.

The alkaline material can be in the form of powder, or in certain instances, liquid, e.g., aqueous, mediums. In the event a liquid alkaline medium is used, liquid mediums of widely varying concentrations prepared from a wide variety of compounds may be used. Dry powdered material, however, is preferred so that less liquid has to be removed during the drying and grinding phase.

The silica gel is contacted with the alkaline material in an amount sufficient to provide a gel having a pH of from about 6 to about 11 and preferably from about 7.5 to about 10.5. The pH is measured in a 5 weight percent aqueous slurry of the gel. The amount of alkaline material used depends on the particular alkaline material used. For example, when sodium carbonate is used, the desired pH is obtained by adding sodium carbonate in amounts of 0.1 to 1.0, and preferably 0.5 to 1.0, percent by weight of the wet hydrogel entering the mill. The hardness of silica gel (a) is defined herein in terms of powder RDA values. The powder RDA's for silica gel (a) is in the range of 100–200.

In a preferred embodiment of this invention, the gel is contacted with a powdered alkaline material as the gel enters the mill. Preferably, the gel is contacted with powdered sodium carbonate. The mill is operated using conventional conditions which are determined by the particular milling equipment used. It is preferred that the alkaline is contacted with the gel at elevated temperatures, e.g., at least 250° C., in order to facilitate rapid interaction of the alkaline material with the gel particles.

As mentioned above, silica gels and precipitated silicas suitable for silica (b) are known to the art. Indeed, preferred embodiments of (b) are conventional dental abrasive silica gel or precipitated silica. The gel can be in the form of hydrogel, aerogel or xerogel, and the moisture content of the gel therefore can vary depending on the type of gel used. U.S. Pat. Nos. 4,303,641 and 4,153,680 describe suitable methods for preparing silica gels, the descriptions of which are incorporated by reference. In general, these gels are prepared by reacting alkali metal silicates with a minimal acid to form a hydrosol, which in turn converts to a hydrogel. The resulting gel is washed and dried using conventional techniques. In general, the gels used for silica (b) preferably will have a water content in the range of 10–60%, and more preferably 15–35% by weight.

Pore structure and other physical properties of silica (b) affect its performance as a dentifrice abrasive. For example, the pH, temperature, and duration of the wash water, as well as the method of drying the gel, influence the physical properties of the silica, such as surface area (SA) and pore volume (PV). Silica gels washed at 65–90° C. at pH's of 8–9 for 15–36 hours and after drying will usually have SA's of 250–400 $m^2/g$ resulting in gels with PV's of 1.0 to 2.1 cc/g. Silica gel washed at pH's of 3–5 at 50–65° C. for 15–25 hours and after drying will have SA's of 700–1,000 $m^2/g$ and form gels with PV's of 0.3–1.3 cc/gram.

Precipitated silicas and methods for making these silicas are also known in the art. Suitable dentifrice-type precipitated silicas are described in U.S. Pat. No. 5,589,160, the contents of which are incorporated by reference. The abrasive performance of dentifrice-type precipitated silicas having surface areas of 25–100 $m^2/g$ and pore volumes of 0.1 to 0.5 cc/g can also be enhanced when used in combination with alkali-hardened silica gels. Surface area, pore volume and pore size distribution measurements mentioned for the gels and precipitated silicas are generated by $N_2$ porosimetric analyses.

Once a particular gel or precipitated silica is selected for silica component (b), the gel or precipitate should be processed to have a median particle size of at least 7 microns, and preferably a median particle size of at least 12 microns. The median particle sizes of dentifrice silicas generally are no larger than 18 microns. Gels or precipitates having this range of particle sizes can be obtained using the milling equipment discussed with respect to preparing silica gel (a).

The hardness for silica (b) is also defined by powder RDA's. The powder RDA's for silica (b) are generally in the range of 50–180. As indicated earlier, it is preferable that the particles of silica (b) are softer. Accordingly, the powder RDA of preferred embodiments of silica (b) is preferably lower than the powder RDA for silica gel (a).

Silica components (a) and (b) are then combined to form the abrasive system of this invention. The weight ratio of (b) to (a) should be at least 1:1 and preferably at least 2:1. In general, the ratio of (b) to (a) should not be greater than 9:1. Therefore, silica (a) should comprise 10 to 50% by weight of an abrasive system consisting of (a) and (b).

Silica components (a) and (b) can be combined prior to being added to a dentifrice composition, or each component can be added to the dentifrice composition separately, as long as the ratios for (b) to (a) mentioned above are maintained.

As indicated earlier, silica (b) preferably is a conventional product and is preferably a dentifrice abrasive which a manufacturer is already using in its compositions. In one embodiment silica (a) can be incorporated into an existing abrasive system in amounts that result in the above ratios of (b) to (a). This highlights one of the advantages of this invention in that it incorporates dentifrice silicas which a dentifrice manufacturer already has in its inventory. In this manner, improved cleaning and abrasion properties compared to the properties obtained with the existing gel or precipitated silica abrasive can be obtained without completely changing from or eliminating existing abrasive systems.

The two silica components (a) and (b) are employed in the dentifrice compositions of this invention in an amount needed to effect cleaning. Generally, silica components (a) and (b) comprise about 5 to about 50 percent, preferably about 10 to about 35 percent, by weight of the dentifrice composition.

The dentifrice of the invention can also contain as optional ingredients a soap or synthetic detergent as a surface tension depressant; flavoring materials; buffers; sweeteners such as saccharin; humectants; preservatives; thixotropic agents such as pyrogenic silica, and harmless coloring materials, in various proportions to give any desired effect. A fluoride such as stannous fluoride, sodium fluoride, sodium monofluorophosphate, zirconium fluoride, or sodium fluosilicate can be included. Each of these fluorine compounds contains available fluoride which can be taken up by the enamel of the teeth. Compounds that are capable of calcium chelation such as phosphates and pyrophosphates are also frequently included constituents of commercial dentifrice formulations. These are conventional components of dentifrices, and materials suitable for this purpose need not be enumerated for they are well known to those skilled in the dentifrice art. U.S. Pat. No. 5,589,160 provides an extensive list of dentifrice components and the contents of that patent are incorporated herein by reference.

In a preferred embodiment, the dentifrice is in the form of a paste, and in this event it will be comprised of the abrasive silica and a humectant and a binder in amounts to give the dentifrice a smooth texture and good flowability. Suitable humectants and binders are known in the art. Suitable humectants include glycerin, sorbitol, ethyl alcohol, mineral oil, corn syrup, glucose and invert sugars, glycols and honey. Glycerin and sorbitol are preferred. Suitable binders include gum tragacanth, sodium carboxymethylcellulose, hydroxyethylcellulose, Indian gum, Irish moss or carrageenan and its derivatives, starch, acacia gums, locust bean gum, pectin and petrolatum. Carbopol™ polymer also is a suitable humectant.

The silica gels and precipitates in the dentifrice compositions of the invention also permits the incorporation of oral health agents such as germicides, antibiotics and astringents. Typical examples include tyrothrycin, triclosan, chlorophyllins, hexachlorophene, the sarcosides and astringent salts.

Such oral health agents are employed in a beneficial amount normally ranging from about 0.01 percent to about 2 percent by weight of paste dentifrice. The humectants are generally employed in an amount from about 5 percent to about 75 percent by weight of the dentifrice, the binders in an amount from about 0.5 percent to about 30 percent by weight of the dentifrice, flavoring agents in an amount from about 0.1 percent to about 5 percent by weight of the dentifrice, water in an amount from about 4 percent to about 60 percent by weight of the dentifrice, surface tension depressants in an amount from about 0.01 percent to about 6 percent by weight of the dentifrice, and preservatives in an amount from about 0.01 percent to about 2 percent of the dentifrice. The dentifrices are prepared by blending the components together, with deaeration being necessary for the translucent and transparent toothpastes.

The unexpected cleaning performance for this invention is shown using conventional abrasion and cleaning tests. For example, dentifrice compositions are typically screened in vitro using the "Stookey Cleaning Test" to determine a composition's efficacy for cleaning and stain removal. This test performs a simulated brushing action typically on more readily available bovine teeth which have been artificially stained. The removal of stain after a brushing operation is quantified by measuring the decrease in color (or blackness) using a colorimeter. Rather than comparing absolute changes in color, the data are usually referenced to that of American Dental Association reference material calcium pyrophosphate (that is, the stain reduction resulting from calcium pyrophosphate use is taken to be by definition 100). Therefore, the cleaning performance of the test compositions will be either below (<100), equal to (=100), or higher (>100) than that obtained using calcium pyrophosphate. This normalized cleaning value is often called the Pellicle Cleaning Ratio (PCR). The higher the PCR the greater the stain removal or "whitening".

Radioactive Dentin Abrasion (RDA) testing measures how the abrasive nature of the dentifrice composition contributes to removal of the softer dentin tissue of the tooth structure. In this test, irradiated dentin is brushed in a manner similar to that described above for cleaning. The amount of dentin that is abraded away from the brushed structure is quantified via radioactive analysis of $^{32}P$ which is observed in the abrasive slurry. In a manner similar to that described for cleaning, the amount of dentin abrasion is referenced to that which occurs with calcium pyrophosphate which is likewise set at 100. The lower the RDA the less abrasive the dentifrice composition.

Radioactive Enamel Abrasion (REA) testing is analogous to RDA testing. The abrasive effect on the enamel which is a harder tissue than dentin is quantified in a likewise manner. In this test irradiated enamel is brushed in a manner similar to that described above for cleaning. The amount of enamel that is abraded away from the brushed structure is quantified via radioactive analysis of $^{32}P$ which is observed in the abrasive slurry. In a manner similar to that described for cleaning, the amount of enamel abrasion is referenced to that which occurs with calcium pyrophosphate. At least two commercial sources, e.g., Indiana University (IU) and Missouri Analytical Laboratories (MAL) perform this test and reference the test data to that of calcium pyrophosphate. However, they set different values for calcium pyrophosphate. IU normalizes to 10 whereas MAL normalizes to 100. The data described herein are supplied by Indiana University. The lower the REA value the less abrasive the dentifrice composition. Dentifrices comprising the combination of silicas (a) and (b) described herein unexpectedly have REA's of less than 30, and in particular less than 10, and most preferably less than 5.

It is also noted that measurements of PCR, RDA and REA are made from samples in powder or paste form. Powder form measurements are taken from the abrasive system in powder form per se. Paste measurements are taken on fully formulated paste compositions into which the abrasives have been incorporated.

The compositions and methods of this invention are illustrated by the following examples.

ILLUSTRATIVE EXAMPLES OF THE INVENTION

Example 1

Preparation and Characterization of Hard Small Silica Component (a)

A hard, small silica component of the invention is prepared using methods disclosed in U.S. Pat. No. 4,303,641. In particular, a conventional acid set hydrogel is washed, dried and coarsely ground before being milled and dried under standard conditions. The moisture content of the silica feed material entering the mill is about 70% by weight.

Sodium carbonate powder is metered into the mill's inlet stream along with the hard small component precursor feed so that as it enters the mill, a constant concentration of alkalinity is maintained in the product.

The resulting milled product is characterized with a median particle size of 2–3 microns and a total volatiles, e.g., moisture, content of about 20% by weight. The small hard silica component has a pH of 8.5 as measured in a 5% by weight aqueous slurry. Powder RDA values measured on a number of batches range from 121 to 139. The particle size distributions for five of the batches of the small hard silica component are provided in Table I. Particle size distributions were measured using a Horiba LA900 laser diffraction analyzer.

TABLE I

Summary of Particle Size Distribution Data on Hard Small Particle Size Abrasive of the Invention Small particle size alkali hardened silica gel

| Particle Size Statistics | Sample B1 | Sample B2 | Sample B3 | Sample B4 | Sample B5 |
|---|---|---|---|---|---|
| Mean, $\mu m$ | 2.42 | 2.29 | 2.30 | 2.49 | 7.01 |
| Std. Dev., $\mu m$ | 1.20 | 1.06 | 1.04 | 1.14 | 3.65 |
| Mode $\mu m$ | 1.78 | 1.73 | 1.77 | 1.89 | 5.39 |

TABLE I-continued

Summary of Particle Size Distribution Data on Hard Small Particle Size Abrasive of the Invention Small particle size alkali hardened silica gel

| Particle Size Statistics | Sample B1 | Sample B2 | Sample B3 | Sample B4 | Sample B5 |
|---|---|---|---|---|---|
| Percentiles | | | | | |
| $d_1$, $\mu m$ | 0.79 | 0.77 | 0.78 | 0.84 | 1.50 |
| $d_2$, $\mu m$ | 0.89 | 0.87 | 0.88 | 0.94 | 1.77 |
| $d_5$, $\mu m$ | 1.06 | 1.04 | 1.05 | 1.12 | 2.32 |
| $d_{10}$, $\mu m$ | 1.24 | 1.21 | 1.22 | 1.31 | 2.97 |
| $d_{50}$, $\mu m$ | 2.16 | 2.07 | 2.10 | 2.27 | 6.39 |
| $d_{90}$, $\mu m$ | 3.90 | 3.62 | 3.63 | 3.97 | 11.76 |
| $d_{95}$, $\mu m$ | 4.69 | 4.29 | 4.26 | 4.66 | 13.84 |
| $d_{98}$, $\mu m$ | 5.82 | 5.22 | 5.10 | 5.57 | 16.58 |
| $d_{99}$, $\mu m$ | 6.73 | 5.95 | 5.74 | 6.26 | 18.62 |
| $d_{99.5}$, $\mu m$ | 7.62 | 6.77 | 6.38 | 6.92 | 20.59 |
| $d_{99.9}$, $\mu m$ | 9.20 | 7.99 | 7.72 | 8.07 | 23.99 |
| Span | 1.23 | 1.17 | 1.15 | 1.17 | 1.37 |
| Skewness | 1.72 | 1.53 | 1.39 | 1.33 | 1.14 |

Notes: All data are determined after two minutes of ultrasonic dispersion. Refractive index ratio = 1.23–4.13I. All statistics above are volume basis.

Example 2

Characterization of Large Soft Silica (b)

Silica (b) illustrated in the Examples below is a conventional silica gel dentifrice abrasive Sylodent® 783 silica, available from Grace Davison of W. R. Grace & Co.-Conn. Typical powder RDA values on this product range from 71 to 89. The particle size of this silica (b) is compared with the harder small particle size silica gel (a) using the Horiba LA900 laser diffraction analyzer. The particle size data for silica (b) are summarized in Table II below.

TABLE II

Summary of Particle Size Distribution Data on Silica Gel (b) Dentifrice Abrasive

| Particle Size Statistics | |
|---|---|
| Mean, $\mu m$ | 16.60 |
| Std. Dev., $\mu m$ | 13.91 |
| Median, $\mu m$ | 12.96 |
| Mode, $\mu m$ | 2.98 |
| Percentiles | |
| $d_1$, $\mu m$ | 1.49 |
| $d_2$, $\mu m$ | 1.76 |
| $d_5$, $\mu m$ | 2.36 |
| $d_{10}$, $\mu m$ | 3.21 |
| $d_{50}$, $\mu m$ | 12.96 |
| $d_{90}$, $\mu m$ | 34.76 |
| $d_{95}$, $\mu m$ | 43.74 |
| $d_{98}$, $\mu m$ | 55.88 |
| $d_{99}$, $\mu m$ | 65.14 |
| $d_{99.5}$, $\mu m$ | 74.12 |
| $d_{99.9}$, $\mu m$ | 91.27 |
| Span | 2.44 |
| Skewness | 1.65 |

Notes: All data are determined after two minutes of ultrasonic dispersion. Refractive index ratio = 1.23–4.13I. All statistics above are volume basis.

Example 3

Dentifrice Composition Comprising Silicas (a) and (b)

A dentifrice composition was prepared using conventional glycerin humectant and other additives such as those disclosed in the Examples of U.S. Pat. No. 5,108,734. Dentifrice Composition No. 1 contains 20% of silica (b) and 10% of silica (a). The particle size of such a blend is summarized in Table III. The abrasive system comprising silicas (a) and (b) is added after humectants are introduced.

TABLE III

Summary of Particle Size Distribution Data on Small Particle Size Hard and Large Particle Size Soft Silicas and Blends Made Therefrom

| Particle Size Statistics ↓ | Small Hard Silica (a) | Large Soft Silica (b) | 4:1* Blend | 2:1* Blend |
|---|---|---|---|---|
| Mean, μm | 2.30 | 16.60 | 9.57 | 10.57 |
| Std. Dev., μm | 1.04 | 13.91 | 8.49 | 9.39 |
| Median, μm | 2.10 | 12.96 | 6.99 | 7.29 |
| Mode, μm | 1.77 | 2.98 | 2.18 | 1.98 |
| Percentiles ↓ | | | | |
| $d_1$, μm | 0.78 | 1.49 | 1.09 | 1.03 |
| $d_2$, μm | 0.88 | 1.76 | 1.26 | 1.18 |
| $d_5$, μm | 1.05 | 2.36 | 1.59 | 1.47 |
| $d_{10}$, μm | 1.22 | 3.21 | 2.02 | 1.84 |
| $d_{50}$, μm | 2.10 | 12.96 | 6.99 | 7.29 |
| $d_{90}$, μm | 3.63 | 34.76 | 20.43 | 24.04 |
| $d_{95}$, μm | 4.26 | 43.74 | 25.98 | 29.07 |
| $d_{98}$, μm | 5.10 | 55.88 | 33.88 | 35.17 |
| $d_{99}$, μm | 5.74 | 65.14 | 40.39 | 39.57 |
| $d_{99.5}$, μm | 6.38 | 74.12 | 47.14 | 43.73 |
| $d_{99.9}$, μm | 7.72 | 91.27 | 60.29 | 52.37 |
| Span | 1.15 | 2.44 | 2.63 | 3.04 |
| Skewness | 1.39 | 1.65 | 1.93 | 1.27 |

Notes: All data are determined after two minutes of ultrasonic dispersion.
Refractive index ratio = 1.23–4.13I. All statistics above are volume basis.
*Ratio of soft:hard silicas.
Large soft silica = Sylodent ® 783 silica.
Both small hard silicas and large soft silicas analyzed by Horiba LA900

Example 4

Dentifrice Composition Comprising Silica Gels (a) and (b)

A dentifrice formulation (Dentifrice Composition No. 2) was prepared similarly to that described in Example 3 except that a version of the alkali hardened abrasive having a median particle size of about 6 microns was substituted for silica (a), which had a median particle size of about 2–3 microns.

Example 5

Dentifrice Composition of Example 1 Except Lower Loading of Silica (b)

A dentifrice formulation (Dentifrice Composition No. 3) was prepared according to the procedure as described in Example 3, except only 11% of silica (b) was included in the formulation, thereby providing weight ratio of silica gel (b) to (a) of about 1:1.

Example 6

Dentifrice Composition of Example 2 Except Lower Loading of Silica (b)

A dentifrice formulation (Dentifrice Composition No. 4) was prepared according to the procedure as described in Example 4, except only 11% of silica (b) was included in the formulation, thereby providing a weight ratio of about 1:1 for silica (b) to silica (a).

Example 7

Control Dentifrice Composition Prepared As Example 1 Comprising Only Silica (b)

A control formulation (Dentifrice Composition No. 5) was prepared according to the procedure as described in Example 3, except only silica (b) was included in the formulation at 30% weight percent loading.

Example 8

Control Dentifrice Composition Prepared as Example 1 but Includes Only Silica (a)

This control formulation (Dentifrice Composition No. 6) was prepared according to the procedure as described in Example 3. Only silica (a) was included in the formulation at 30% weight percent loading.

Example 9

Cleaning, RDA and REA Results

The cleaning and abrasive performances of the pastes described in Examples 2–8 are tabulated in Table IV. The RDA, PCR and REA values shown were obtained from the paste.

TABLE IV

Summary of Cleaning and Abrasion Tests

| Dentifrice Composition Number | Silica Loading % (b)/% (a) | Range of Pellicle Cleaning Ratios | Range of Radioactive Dentin Analyses | Radioactive Enamel Analysis |
|---|---|---|---|---|
| 1 | 20/10* | 87–149 (115) | 99–140 | 3.92 |
| 2 | 20/10** | 122 (122) | 105 | 3.56 |
| 3 | 11/10* | 109–132 (121) | 78–100 | 3.12 |
| 4 | 11/10** | 111 (111) | 85 | 2.82 |
| 5 | 30/0 | 84–102 (92) | 139–177 | 1.6–2.6 |
| 6 | 0/30 | 100–111 (106) | 123 | — |

*Silica (a) had a median particle size of 2–3 microns
**Silica (a) had a median particle size of about 7 microns
Number in () are averages
— not measured The data show that when silicas (a) and (b) are combined as in Dentifrice Compositions 1 and 2 at the same total weight loading of abrasive, those compositions generally reach higher levels of cleaning than the same loading of silicas (a) or (b) when used singly as noted by Dentifrice Compositions 5 and 6. Also of note is the unexpectedly lower RDAs when one compares compositions 1–4 versus 5 and 6. The effect of particle size on RDA is also apparent as compositions 1 and 3, which include the smaller particle size hard silica, are 6–7 points lower in RDA than the counterpart dentifrices which contain a larger particle size hard silica. The conclusion from these data is that improvements in cleaning with diminished soft tissue abrasion result unexpectedly from combining a small particle size hard silica with a softer larger particle size silica. Hard tissue (i.e., enamel) abrasion as measured by Radioactive Enamel Abrasion (REA) is not significantly increased and is quite low when compared to commercial whitening type dentifrice compositions some of which have REA values as high as 30 and many which exceed 10.

What is claimed is:
1. A dentifrice composition comprising humectant and a silica abrasive system, said abrasive system comprising
   (a) silica gel (i) having a median particle size below about 7 micron, (ii) a pH of from about 6 to about 11, and (iii) a hardness defined by a powder RDA of 100 to 200, and a PCR of 100 to about 150 when said silica (a) is formulated by itself into a dentifrice paste; and (b) silica gel or precipitate having a median particle size of about 7 microns or greater and having a hardness defined by a powder RDA of about 50 to 180 and a PCR of about 80 to about 105 when said silica (b) is formulated by itself into a dentifrice paste;

wherein particle sizes are determined by laser diffraction and further wherein the weight ratio of (b) to (a) is at least 1:1, and the dentifrice composition comprising (a) and (b) has an RDA of about 150 or below, and a PCR of at least 80, and up to about 150, and an REA of less than about 30, as measured on the IU scale.

2. A dentifrice composition of claim 1 wherein silica gel (a) has a median particle size of less than 4 microns.

3. A dentifrice composition of claim 1 wherein the composition has an REA of less than 10.

4. A dentifrice composition of claim 1 wherein silica gel (a) is hydrous silica gel with a pH of from about 7.5 to about 10.5 as measured in an aqueous slurry containing 5% by weight silica.

5. A dentifrice composition of claim 1 wherein the silica gel (a) is prepared by contacting a hydrous gel with an alkaline medium.

6. A dentifrice composition of claim 4 wherein the silica gel (a) is prepared by contacting a hydrous gel with sodium carbonate.

7. A dentifrice composition of claim 2 wherein silica gel or precipitate (b) has a median particle size of at least 12 microns.

8. A dentifrice composition of claim 7 wherein the weight ratio of (b) to (a) is at least 2:1.

9. A dentifrice composition of claim 1 wherein silica gel (a) has a total volatiles content in the range of about 5–30% by weight of silica gel (a).

10. A dentifrice composition of claim 4 wherein the median particle size of silica gel (a) is less than 4 microns, the median particle size of silica gel or precipitate (b) is at least 12 microns and the weight ratio of (b) to (a) is at least 2:1.

11. A dentifrice composition of claim 1 wherein the silica abrasive system comprises about 5 to about 50% by weight of the total dentifrice composition.

* * * * *